United States Patent [19]

Nagl et al.

[11] 4,218,219

[45] Aug. 19, 1980

[54] CONDENSATION PRODUCT FROM PHENOTHIAZINE AND P-NITROSOPHENOL, PROCESS FOR THE PRODUCTION OF THE CONDENSATION PRODUCT, PROCESS FOR THE PRODUCTION OF SULFUR DYESTUFFS USING THE CONDENSATION PRODUCT AND THE SULFUR DYESTUFFS PREPARED THEREWITH

[75] Inventors: Gert Nagl, Frankfurt am Main; Joachim Ribka, Offenbach am Main-Bürgel; Heinz Dickmanns, Frankfurt am Main; Ulrich Gotsmann, Bergen-Enkheim, all of Fed. Rep. of Germany

[73] Assignee: Cassella Aktiengesellschaft, Frankfurt am Main, Fed. Rep. of Germany

[21] Appl. No.: 955,643

[22] Filed: Oct. 30, 1978

[30] Foreign Application Priority Data

Oct. 29, 1977 [DE] Fed. Rep. of Germany ....... 2748744

[51] Int. Cl.[2] ...................... C09B 21/00; C09B 49/06; C07D 279/18

[52] U.S. Cl. .......................................... 8/652; 544/37

[58] Field of Search ................ 544/37; 260/317; 8/34, 8/35, 37, 178 R

[56] References Cited

U.S. PATENT DOCUMENTS

| | | | |
|---|---|---|---|
| 966,092 | 8/1910 | Herz | 260/317 |
| 1,128,370 | 2/1915 | Schmidt et al. | 260/317 |
| 1,867,863 | 7/1932 | Muth | 544/37 X |

OTHER PUBLICATIONS

Lubs, The Chemistry of Synthetic Dyes and Pigments, pp. 321 to 323, Reinhold Pub. Corp., NY (1955).

Dutt, J. Chem. Soc., vol. 125, pp. 802 to 807 (1924).

Hackh's Chemical Dictionary, Fourth Ed., p. 648, McGraw-Hill (NY), 1969.

Beilsteins Handbuch der Organischen Chemie, Mainwerke, vol. 27, 4th Ed., pp. 63, 64, 65 and 67-68, System No. 4198, Verlag Von Julius Springer, Berlin, Germany (1937).

Beilsteins Handbuch der Organischen Chemie, 4th Ed., Erstes Erganzungswerke, p. 226, System No. 4198, Verlag Von Julius Springer, Berlin, Germany (1938).

*Primary Examiner*—John D. Randolph

*Attorney, Agent, or Firm*—Connolly, Bove & Lodge

[57] ABSTRACT

Green sulfur dyestuff is produced by reacting phenothiazine in sulfuric acid with an oxidizing agent, condensing the oxidized phenothiazine with p-nitrosophenol and thionating with sulfur and sodium sulfide the condensate in a bake or reflux process.

10 Claims, No Drawings

CONDENSATION PRODUCT FROM PHENOTHIAZINE AND P-NITROSOPHENOL, PROCESS FOR THE PRODUCTION OF THE CONDENSATION PRODUCT, PROCESS FOR THE PRODUCTION OF SULFUR DYESTUFFS USING THE CONDENSATION PRODUCT AND THE SULFUR DYESTUFFS PREPARED THEREWITH

The present invention is concerned with a condensation product from phenothiazine and p-nitrosophenol which contains an indophenol-S-oxide I with a proportion of not less than 60 percent-by-weight of the formula

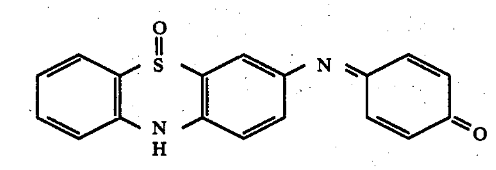

(I)

as well as a process for its production. Furthermore the present invention relates to a process for the production of sulfur dyestuffs and the sulfur dyestuffs obtained therewith.

According to "Journal of the Chemical Society, London", volume 125, pages 802 and 803 (1924) it is possible to condense phenothiazine in concentrated sulfuric acid with p-nitrosophenol and to melt the condensation product obtained with sulfur and sodium sulfide at 250° to 300° C. to form green sulfur dyestuffs The sulfur dyestuffs produced in this manner, however, show a number of serious disadvantages, especially poor yield, low dyeing strength, poor solubility in alkali dithionite and sulfide vats, dull shades, non-uniform occurrence in the production batches, low fastness, especially fastness to wet processing and fastness to washing with peroxide, because of which they have so far not been introduced into practical use.

In order to obtain green sulfur dyes it has, therefore, been necessary hitherto either to use derivatives of copper phthalocyanine containing sulfur which cannot be used from a sodium dithionite vat and whose use is therefore limited and whose production is comparatively troublesome technically, which renders their utilization considerably more expensive, or else to fall back on green sulfur dyestuffs, such as for example Sulfur Green 2, C.I. No. 53 571, or Sulfur Green 3, C.I. No. 53 370, but which have poor wet fastness properties, especially a poor fastness to washing with peroxide and, therefore, cannot be used for dyeing with a high degree of fastness.

Therefore, there has been an urgent requirement for a process which makes it possible in a simple technical manner to produce sulfur dyestuffs of a high purity, good solubility, good yield and great coloring power which give green dyeings on cotton material.

Surprisingly, it has now been found that this problem can be solved, if such condensation products from phenothiazine and p-nitrosophenol are thionated by the bake or reflux process, which contain indophenol-S-oxide of formula I with a proportion of not less than 60 percent-by-weight.

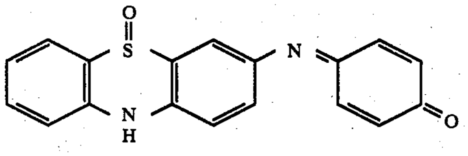

(I)

Condensation products of this type are made according to the process of the present invention by reacting phenothiazine with p-nitrosophenol in sulfuric acid. The process of the present invention is characterized by oxidizing the phenothiazine before or during the condensation with p-nitrosophenol in the presence of an additional oxidizing agent.

In the process hitherto known, according to which the phenothiazine is reacted with 1 mole of p-nitrosophenol in concentrated sulfuric acid, it is mainly the sulfuric acid employed as solvent that acts as oxidizing agent. Unlike this, the process of the present invention uses, in addition to the sulfuric acid and 1 mole p-nitrosophenol employed, an additional oxidizing agent.

Such oxidizing agents as additionally used can be inorganic or organic agents. Suitable inorganic oxidizing agents are, for example, halogens, such as chlorine or bromine, nitrogen oxides, nitrous acid, nitric acid or peroxides and salts of per acids, in particular hydrogen peroxide. Of particular advantage is the use of sulfur trioxide as additional oxidizing agent which is suitably employed in the form of fuming sulfuric acid (oleum) with a proportion of appr. 65 percent-by-weight of sulfur trioxide. When using sulfur trioxide, one should dissolve the phenothiazine advantageously in 100% concentrated sulfuric acid.

Suitable organic oxidizing agents are, for instance, peroxy carboxylic acids, such as for example peroxy acetic acid, quinones, such as benzoquinone, tetrachloro-benzo-quinone or dicyanodichlorobenzoquinone. Para-nitrosophenol may also be used as additional oxidizing agent.

Theoretically, the process of the present invention necessitates one oxidation equivalent of the additional oxidizing agent being used in order to effect the complete oxidation of one mole of the phenothiazine. As a rule, good results are obtained by using at least 0.5 oxidation equivalent of the additional oxidizing agent. In the case of the sulfur trioxide preferably used as additional oxidizing agent one oxidation equivalent is equal to 0.5 mole. One oxidation equivalent p-nitrosophenol is equal to 0.25 mole. The p-nitrosophenol of the process of the present invention acting as additional oxidizing agent and condensating agent for the oxidized phenothiazine, a total of not less than 1.125 moles of the p-nitrosophenol, referred to one mole phenothiazine, are required. It has turned out that very good results are achieved when using a total of not less than 1.2 moles of the p-nitrosophenol.

It may be assumed that at first the phenothiazine is oxidized by the sulfuric acid to give a radical cation, in which case water is formed, and when the radical cation is further oxidized with the additional oxidizing agent to give a dication, water is likewise formed. In the event that an oxidizing agent is actually used which reacts with water, as does sulfur trioxide, the reaction water must be bonded with other media, for instance by adding phosphorus pentoxide or a correspondingly larger excess of additional oxidizing agent must be employed. If no other agent for bonding the reaction-water is used, two moles of the sulfur trioxide are used to effect the complete oxidation and bonding of the reaction water.

If the phenothiazine is not dissolved in concentrated sulfuric acid but is added to a solution of the p-nitrosophenol in a more diluted sulfuric acid, the radical cation is formed only slowly through reaction with the dilute sulfuric acid and a larger excess of p-nitroso-phenol is requisite.

A certain disadvantage of using organic oxidizing agents consists in the fact that the reduced forms of these compounds or their subsequent products are later to be found in the reaction mixtures and have to be removed either from the isolated condensation products of the present invention or else from the effluents. Therefore, efforts will be made to keep this excess as low as possible when using an excess of additional oxidizing agent. Normally, it will not be necessary to utilize an excess of more than four oxidation equivalents when employing an organic oxidizing agent. Thus, if p-nitrosophenol is used it is normally not necessary to use in all more than two moles for an additional oxidizing and condensating agent.

If the sulfur trioxide being preferred as additional oxidizing agent is used, no impurities of the condensation products or no further waste water problems occur even if a larger excess is used. Although there is no harm in using a major excess of sulfuric trioxide, it will, normally, be unnecessary to employ more than 10 moles of sulfuric trioxide.

It is quite normal to carry out the oxidation of the phenothiazine in a sulfuric acid of an at least 60% concentration advantageously, however, in one of at least 80%, preferably in one of 90 to 100% concentration and suitably at temperatures of −40° to +40° C., preferably at 0° to 25° C. Normally, oxidation requires cooling.

The oxidation being complete, the condensation of the oxidation product with p-nitrosophenol is effected in accordance with the present invention in a sulfuric acid of a 60 to 90%, preferably 75 to 82% concentration. If the oxidation of the phenothiazine is carried out in concentrated sulfuric acid, for example the latter is suitably diluted by the addition of ice. The condensation is advantageously effected at temperatures of −20° to 20° C., preferably of −10° to +10° C. The reaction is slightly exothermic so that the desired reaction temperature must be maintained by cooling. The isolation of the resulting condensation products is done in the conventional manner, for example by pouring the reaction mixture into water, by filtering off, washing, neutralizing and drying.

The percentage amounts of the concentration given for the sulfuric acid only relate within the scope of the present invention to the quantity of the components water and sulfuric acid in the reaction mixtures. When calculating the concentration of sulfuric acid it is necessary to also consider the consumption of the sulfuric acid and the formation of the reaction water.

When using the p-nitrosophenol likewise as additional oxidizing agent, the additional oxidation and the condensation occur simultaneously. This simultaneous oxidation and condensation is advantageously effected in sulfuric acid with a 60 to 90%, preferably 75 to 82% concentration. In order to keep the required quantity of the additional oxidizing agent as low as possible, it is advisable to dissolve at first the phenothiazine in concentrated sulfuric acid and to dilute this solution before adding the para-nitrosophenol to obtain a sulfuric acid concentration of 60% to 90%, preferably 75 to 82%.

The application of an additional oxidizing agent in accordance with the present invention and the carrying out of the condensation between the oxidized phenothiazine and the p-nitrosophenol in sulfuric acid of a 60 to 90%, preferably 75 to 82% concentration results astonishingly in a high yield of products which only contain very small proportions of these by-products whose presence leads to a reduction in the quality of the sulfur dyes obtained. Thus, the condensation products of the present invention are practically free from unreacted phenothiazine and the total of the chemically undefined by-products is below 20%, as a rule even below 10%. The main component of the condensation products of the present invention is indophenol-S-oxide I with a proportion of 60 to 100%, preferably 80 to 100 percent-by-weight and especially 90 to 100 percent-by-weight. In addition, the condensation products of the present invention contain indophenol Ia with a proportion of 0 to 40 percent-by-weight, preferably 0 to 20 percent-by-weight and in particular 0 to 10 percent-by-weight.

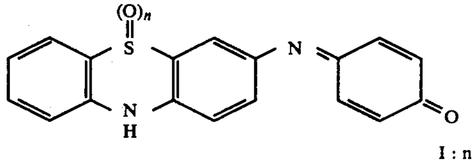

I : n = 1
Ia : n = 0

Condensation products obtained starting from phenothiazine and p-nitrosophenol having such a high content of indophenol-S-oxide of formula I are new, for it had so far not been possible to produce them according to condensation methods hitherto known in the art. Indophenol-S-oxide of formula I can also occur wholly or partly in its tautomeric forms.

The condensation products of the present invention are converted in a manner known per se into sulfur dyestuffs by thionation in the bake or reflux process, which, when applied onto cotton, give green dyeings and, onto polyamide, green to black dyeings. These thionating processes are, for instance, described in "Venkataraman, The Chemistry of Synthetic Dyes, vol. 2 (1952), page 1062 et seq. and page 1103 et seq. as well as vol. 7 (1974), page 24 et seq., Academic Press, New York, San Francisco, London".

Preferably, the thionation of the condensation products of the present invention is carried out according to the reflux process.

Particularly suitable are reflux processes which operate using alkali polysulfide, when per mole of the product to be thionated one uses 2 to 6 moles, preferably 2.5 to 4 moles, of sodium sulfide and 7 to 30 moles, preferably 13 to 18 moles, of sulfur. They are carried out in the solvents which are usual for thionation reflux methods. As solvent in which it is advantageously possible to operate, one may mention alkanols or cyclo alkanols with 1 to 7 carbon atoms, such as for example methanol, ethanol, propanol, isopropanol, n-butanol, isobutanol, amyl alcohol, cyclohexanol, methylcyclohexanol and monoalkyl ether, especially monoalkyl ethers of ethyleneglycol and diethyleneglycol as well as, for example, ethyleneglycol mono-methyl ether, mono-ethyl ether, monopropyl ether, diethyleneglycol monomethyl ether, monoethyl ether and monopropyl ether.

The thionation of the condensation products can be carried out with the exclusion of water or in a purely aqueous medium, but is normally carried out in solvents containing water with a water content of from 5 to 70%. In the case of solvents which are miscible with water, one preferably operates using the usual hydrotropic compounds, for example the sodium salts of xylenesulfonic acid.

The reflux process is carried out at temperatures of 80° to 300° C., preferably 100° to 180° C., and especially in the range from 105° to 130° C., and, advantageously, with a period of reaction of 1 to 100, preferably 20 to 80 hours.

In the thionation of the condensation products made according to the invention by the bake process, these are heated with 7 to 30 times the molar quantity of sulfur and 2 to 6 times the molar quantity of sodium sulfide for 1 to 20 hours to 200° to 300° C. Here again one can operate first of all in the solvent, preferably in water in order to ensure a good homogeneity of the reaction mixture. The solvent is then evaporated off and the solvent-free melt is, advantageously, heated to the desired temperature in an atmosphere of protective gas.

If instead of the crude phenothiazine-p-nitrosophenol condensation products made according to the invention one thionates the compounds I and Ia, isolated therefrom, in a known manner as stated above, one also obtains green sulfur dyestuffs of the invention. It is also possible to produce the green sulfur dyestuffs according to the invention by thionating the leuco compound of indophenol Ia of the formula

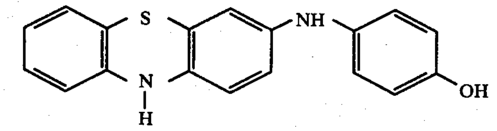

or from crude reduction products of the condensation products made according to the invention, which predominantly contain this leuco compound.

The reduction of the condensation products can be carried out with the usual reducing agents in a known manner, for example with sodium hydrogen sulfide at 50° to 80° C. It is to be assumed that also during the thionation of the condensation products of the invention at least a part of the condensation products is first of all reduced and only then does it take up sulfur.

The sulfur dyestuffs produced by the process according to the invention can be isolated in the usual manner and then brought into the various commercial forms.

If the thionation has been carried out in a solvent which is miscible with water in the presence of hydrotropic compounds, the melt can also be further processed direct to liquid dyestuffs ready-for-use without isolating the dyestuff.

The sulfur dyestuffs produced according to the invention can be very easily reduced by reducing agents, such as sodium dithionite or alkali sulfide and in this way give clear aqueous solutions. They can be used for dyeing vegetable fibers and polyamide by the usual processes known for dyeing with sulfur or sulfur vat dyestuffs.

For this purpose they are converted with reducing agents, such as for example sodium formaldehyde sulfoxylate, glucose or preferably sodium dithionite, sodium sulfide or sodium hydrogen sulfide, into the soluble leuco form which is applied on to the fibers. The dyestuffs occurring in the liquid form ready-for-use contain the soluble leuco form and reducing agents and can be used for dyeing the abovementioned fibers without any further addition of reducing agents.

After the application of the dyestuffs on to the fibers the leuco form of the sulfur dyestuffs of the invention is converted once again into the insoluble form of the sulfur dyestuff in the usual manner, for example by "hanging" the dyed products in the air or oxidizing them with oxidizing agents, such as for example hydrogen peroxide, alkali chlorite or alkali iodate. The sulfur dyestuffs which can be produced according to the invention dye the cellulose to full green shades.

On cellulose fibers the dyestuffs of the invention have in particular been found to give the following advantages, as compared with the nearest shades of commercial products Sulfur Green 2, C.I. No. 53 571, and Sulfur Green 3, C.I. No. 52 570: very good fastness to light, very good fastness to wetness, very good fastness to washing with peroxide according to DIN 54 015 and good fastness to mercerising.

On polyamide, according to the reducing agent and the quantity of dyestuff used, one obtains green to black shades. By using an adequate quantity of dyestuff—as a rule 3 to 4%, related to the weight of fiber—using sodium hydrogen sulfide as reductant, it is possible to obtain black shades with very good fastness properties on polyamide. The dyestuffs particularly show a very good fastness to light and very good fastness to wetness. As compared with the commercial product Color-Index Sulfur Black 11, C.I. No. 53 290, the new dyestuffs on polyamide, inter alia, show the advantage of easier oxidizability so that by oxidation with hydrogen peroxide one obtains perfect black dyeing without any tendency to bronzing.

A further advantage of the dyestuffs of the invention is to be seen in their stability to the action of alkali dithionite and alkali formaldehyde sulfoxylate as well as the fact that they can be produced by a simple technical process.

As compared with the sulfur dyestuffs prepared according to the very general statements made in the "Journal of the Chemical Society, London" 125, pages 802 and 803, the dyestuffs of the invention are characterised by considerably improved fastness properties, especially by better fastness to wet processing and better fastness to washing with peroxide, by their clearer shades, considerably improved solubility in alkali dithionite and sulfide vats, more uniform results of the production batches, greater dyeing strength, improved affinity and considerably higher dye yield.

In the Working Examples which follow, "parts" are parts by weight and all the percentages are percentages by weight.

EXAMPLE 1

40 parts of phenothiazine are dissolved at room temperature in 160 parts of 100% sulfuric acid whilst cooling. Then 80 parts of fuming sulfuric acid with a content of 62.5 percent-by-weight of free $SO_3$ is added drop by drop whilst cooling at room temperature. After continuing to stir for one hour and whilst cooling at room temperature there are added drop by drop 23 parts of 48 percent sulfuric acid and 38 parts of ice. Then the solution is cooled to minus 5° C. and, whilst cooling and vigorously stirring, one adds 30.5 parts of aqueous 85% p-nitrosophenol paste. The reaction mixture is stirred for a further 4 hours whilst cooling at 0° C. It is then poured into a vigorously stirred mixture of 200 parts of water and 400 parts of ice. The product is filtered with suction, washed with approximately 500 parts of water, brought into a suspension with water, neutralized with caustic soda solution, filtered with suction again, washed free from salt, dried and milled. One obtains about 64 parts of a condensation product with a content of about 93 percent-by-weight of the compound of formula I (determination of the content by potentiometric titration using titanium trichloride) and less than 0.5 per cent-by-weight of phenotiazine.

Analysis calculated for indophenol I: ($C_{18}H_{12}N_2O_2S$). Calculated: C: 67.5%, H: 3.75%, N: 8.75%, O: 10%, S: 10%. Found: C: 66.8%, H: 3.6%, N: 8.4%, O: 11%, S: 10.3%.

The IR spectrum shows characteristic absorption bands at approximately 1345 $cm^{-1}$, 735 $cm^{-1}$ and at approximately 1125 $cm^{-1}$.

The product dissolves in dimethylformamide and tetramethylenesulfone with a red color. The ethanolic solution has an absorption maximum at 530 mm in the visible range.

The same product as above is obtained if the fuming sulfuric acid is placed in the vessel first of all together with the 100% sulfuric acid, the phenothiazine is added to it, whilst cooling at 20° to 25° C., and otherwise the processing is carried out in accordance with this Example. EXAMPLE 2

40 parts of phenothiazine are dissolved in 250 parts of concentrated sulfuric acid whilst cooling at room temperature. Whilst cooling at room temperature, one adds 47 parts of ice. Then the solution is cooled to −5° C. and, whilst cooling and vigorously stirring, one adds 36.5 parts of aqueous 85% p-nitrosophenol paste. (Molar ratio phenothiazine:p-nitrosophenol 1:1.25 ) The reaction mixture is stirred for a further 4 hours whilst cooling at 0° C. It is then poured into a vigorously stirred mixture of 1000 parts of water and 700 parts of ice. The product is filtered with suction, washed with approximately 500 parts of water, mixed into a suspension with water, neutralized with caustic soda solution, filtered with suction again, washed free from salts, dried and ground. Obtained are approximately 61 parts of a condensation product with a content of approximately 93 percent-by-weight of the compound I (determination of the content by potentiometric titration using titanium trichloride) and about 2 percent-by-weight of phenothiazine.

Analysis, calculated for indophenol I: ($C_{18}H_{12}N_2O_2S$). Calculated: C: 67.5%; H: 3.75%; N: 8.75%; O: 10%; S: 10%. Found: C: 67.3%; H: 3.7%; N: 8.8%; S: 10.3%.

The IR spectrum, the absorption spectrum in the visible range and the color of the solution agree with the product of Example 1.

EXAMPLE 3

(Comparative Example to Example 2)

40 parts of phenothiazine are dissolved at room temperature in 250 parts of concentrated sulfuric acid whilst cooling at room temperature. The solution is cooled to −5° C. and, whilst cooling and vigorously stirring, one adds 30.5 parts of aqueous 85% p-nitrosophenol paste (molar ratio phenothiazine:p-nitrosophenol=1:1.05. The reaction mixture is stirred for a further 4 hours whilst cooling at 0° C. It is then poured into a vigorously stirred mixture of 1000 parts of water and 700 parts of ice. The product is filtered with suction, washed with approximately 500 parts of water, taken up into a suspension with water, neutralized with sodium hydroxide solution, filtered with suction again, washed free from salt, dried and milled.

Obtained are approximately 52 parts of a product with a content of about 4 percent-by-weight of phenothiazine.

According to the method of determination by titration using $TiCl_3$ one obtains approximately the following figures:

approx. 35 percent-by-weight for the compound of formula I and approx. 40 percent-by-weight for the compound of formula Ia.

To the extent of approx. 20%, the product obtained consists of undefined organic compounds.

EXAMPLE 4

43.5 parts of aqueous 85% p-nitrosophenol paste are placed, whilst cooling, in 300 parts of 80% sulfuric acid at 0° C. and dissolved. Into this solution, whilst cooling, there are sprinkled 40 parts of powdered phenothiazine at −10° to 0° C. whilst vigorously stirring, and uniformly mixed in (molar ratio phenotiazine:p-nitrosophenol=1:1.5). The reaction mixture is stirred for a further 4 hours whilst cooling at 0° C. Then the reaction mixture is poured into a vigorously stirred mixture of 1000 parts of water and 700 parts of ice. The product is filtered with suction, washed with approx. 500 parts of water, taken up into a suspension with water, neutralized with sodium hydroxide solution, filtered with suction again, washed free from salt, dried and milled. Obtained are about 64 parts of a condensation product with a content of about 85 percent-by-weight of the compound of formula I (determination of the content by potentiometric titration using titanium trichloride) and about 0.5 percent-by-weight of phenothiazine.

Analysis, calculated for indophenol I: ($C_{18}H_{12}N_2O_2S$). Calculated: C: 67.5%, H: 3.75%, N: 8.75%, O: 10%, S: 10%. Found: C: 66.8%, H: 3.5%, N: 8.5%, O: 10.6%, S: 10.3%.

The IR spectrum, the absorption spectrum in the visible range and the color of the solution agree with the product of Example 1.

EXAMPLE 5

(Comparative Example to Example 4)

30.5 parts of aqueous 85% p-nitrosophenol paste are introduced, whilst cooling, into 250 parts of concentrated sulfuric acid at below 0° C. and dissolved. Into this solution there are sprinkled, whilst cooling, 40 parts of powdered phenothiazine at −10° to 0° C., whilst vigorously stirring, and uniformly mixed (molar ratio phenothiazine:p-nitrosophenol=1:1.05).

The reaction mixture is stirred for a further 4 hours whilst cooling at 0° C. Then the reaction mixture is poured into a vigorously stirred mixture of 1000 parts of water and 700 parts of ice. The product is filtered with suction, washed with approximately 500 parts of water, taken up into a suspension with water, neutralized with sodium hydroxide solution, filtered with suction again, washed free from salt, dried and milled. Obtained are approximately 50 parts of a product with a content of approximately 4 percent-by-weight of phenothiazine. According to the method of determination by titration using $TiCl_3$, one obtains approximately the following figures:

approx. 35% by weight for the compound of formula I and approx. 35 percent-by-weight for the compound of formula Ia.

EXAMPLE 6

40 parts of the product of Example 1 are stirred into 800 parts of a 10% aqueous solution of sodium hydrogen sulfide at a temperature of about 70° C. It is vigorously stirred for a further 3 hours at 70° C., cooled to room temperature and the light-colored reduced product is filtered with suction and washed. The filter cake is taken up into a suspension with water, adjusted so as to be slightly acid using hydrochloric acid, filtered with suction again, washed and dried. Obtained are about 33 parts of the leuco compound.

Analysis calculated for the leuco compound of indophenol I: ($C_{18}H_{14}N_2OS$). Calculated: C: 70.59%; H: 4.57%; N: 9.15%; O: 5.23%; S: 10.46%. Found: C: 69.5%; H: 4.4%; O: N: 9.1%; 6.0%; S: 10.9%.

The product is very sparingly soluble both in alkaline aqueous solutions of sodium dithionite and also in aqueous solutions of sodium sulfide and sodium hydrogen sulfide. The IR spectrum shows characteristic absorption bands at 1600, 1495, 1465, 1300, 1235 and 735 $cm^{-1}$. The absorption bands at 763 $cm^{-1}$ common to both compounds of formulae I and Ia and also the absorption bands of the compound of formula I at 1125 and 1345 $cm^{-1}$ are lacking.

EXAMPLE 7

44 parts of the product of Example 1 are introduced into a polysulfide solution at about 70° C. prepared from 205 parts of 95% n-butanol, 49 parts of flake sodium sulfide (60%) and 58 parts of sulfur. It is heated to the boil and the mixture is maintained for 72 hours under a reflux with vigorous boiling and agitation. Without cooling, one adds 2.5 parts of sodium nitrite and 25 parts of 95% n-butanol and stirring is continued for a further 2 hours under a reflux. Then one adds 300 parts of brine of 24° Bé and the butanol is distilled off with steam. The dyestuff is filtered with suction and washed free from polysulfide with brine of 12° Bé. The filter cake is taken up in hot water to form a suspension, adjusted to a pH of 2 with hydrochloric acid and stirring is then continued for 1 hour at 60° C. Then it is filtered with suction, washed until neutral, dried and milled. Obtained are about 61 parts of dyestuff in powder form. It dyes the cellulose fibers from alkali sulfide or alkali dithionite solution in green shades of very good fastness to wet processing and to light and polyamide in green to deep black shades of very good fastness to wet processing and light.

The dyestuff is excellently soluble in dithionite, sulfide and hydrogen sulfide vats.

If instead of the product of Example 1 44 parts of the product of Example 6 are used a dyestuff with practically the same properties is obtained.

If instead of the product of Example 1 44 parts of the products of Example 2 or Example 4 are used dyestuffs with practically the same properties but with a somewhat lower solubility are obtained.

EXAMPLE 8

(Comparative Example to Example 7)

If in Example 7 one uses instead of the product of Example 1 44 parts of the product of Example 3 and operates otherwise in accordance with the instructions of Example 7, about 60 parts of dyestuff in powder form are obtained. The dyestuff differs from that of Example 7 in having a considerably lower dyeing strength, distinctly duller shades and considerably poorer solubility in dithionite, sulfide and hydrogen sulfide vats.

EXAMPLE 9

(Comparative Example to Example 7)

If in Example 7 instead of the product of Example 1 one uses 44 parts of the product of Example 5 and operates otherwise in accordance with the instructions of Example 7, about 60 parts of dyestuff in powder form are obtained. The dyestuff differs from that of Example 7 by its considerably lower dyeing strength, the distinctly duller shades and the considerably poorer solubility in dithionite, sulfide and hydrogen sulfide vats.

EXAMPLE 10

44 parts of the product of Example 1 are introduced into a polysulfide solution at about 70° C. which has been produced from 50 parts of water 50 parts of diethyleneglycolmonoethyl ether, 30 parts of the sodium salt of m-xylenesulfonic acid, 49 parts of flake sodium sulfide (60%) and 58 parts of sulfur. It is heated to the boil and the mixture is maintained boiling vigorously, whilst stirring under a reflux, for 72 hours. The fused mass is then brought into solution by the addition of 42 parts of the sodium salt of m-xylenesulfonic acid, 160 parts of a 30% sodium hydrogen sulfide solution, 53 parts of flaky sodium sulfide and 250 parts of water. Obtained is a water-thin, clear non-settling stale solution of the reduced sulfur dyestuff, which is miscible with water without precipitation. With this dyestuff solution ready-for-use and without any further addition of reducing agents one obtains on cellulose fiber green colors of very good fastness to wet processing and to light, on polyamide fiber green to deep black colors of good fastness to wet processing and to light. The dyestuff in this form is particularly suitable for use in dyeing processes operating continuously.

If instead of the product of Example 1 44 parts of the products of Examples 2, 4 or 6 are used, dyestuffs with practically the same properties are obtained.

EXAMPLE 11

(Comparative Example to Example 10)

If in Example 10 instead of the product of Example 1 one uses 44 parts of the product of Example 3 and proceeds according to the instructions of Example 10, a dyestuff is obtained which differs from the dyestuff of Example 10 by the considerably lower dyeing strength, the considerably duller shades and the considerably poorer solubility.

EXAMPLE 12

(Comparative Example to Example 10)

If in Example 10 instead of the product of Example 1 one uses 44 parts of the product of Example 5 and operates otherwise in accordance with the instructions of Example 10, a dyestuff is obtained which differs from the dyestuff of Example 10 in the considerably lower dyeing strength, the distinctly duller shades and the appreciably poorer solubility.

EXAMPLE 13

(Comparative Example to Examples 7 and 10)

From 49 parts of flaky sodium sulfide, 58 parts of sulfur and 170 parts of water one prepares a polysulfide solution. Into this solution, whilst warm, one stirs 44 parts of the product of Example 3 and then concentrates the reaction mixture by evaporation whilst stirring. After the water has been evaporated the reaction mixture is heated within 4 hours to a temperature of 250° C. and it is then maintained at this temperature for a further 4 hours. After cooling, the product is milled. Obtained are about 110 parts of dyestuff. This dyestuff differs from those of Examples 7 and 10 by the quite considerably yellower shade (olive), the considerably lower dyeing strength, the poorer solubility and particularly by the very much poorer fastness to wet processing, especially the considerably poorer fastness to washing with peroxide.

EXAMPLE 14

In a dyeing cup which is held in a heatable bath, one stirs 0.2 parts of the dyestuff produced according to Example 7 with 0.05 parts of the anion-active wetting agent ® Nekal BX (Supplier: BASF AG, Germany) and 3 parts of 18% sodium hydroxide solution, one then adds 200 parts of water at 70° C. and 0.8 parts of sodium dithionite and one stirs the vat until the dyestuff gives a clear solution. In the finished dye liquor one keeps 10 parts of cotton material at 60° C. for 45 minutes so that it is constantly in motion. The dyed cotton material is then taken from the liquor and any liquor still adhering to it is squeezed off. Then the dyed material is rinsed thoroughly with cold water. It is immediately placed in a solution at a temperature of 40° C. of 0.23 parts of a 35% aqueous hydrogen peroxide solution and 1 part of sodium dihydrogen phosphate in 200 parts of water, which had previously been adjusted to a pH of 8 with sodium hydroxide solution. The dyed cotton material is maintained in motion for 15 minutes at 40° C. in the oxidation bath, then it is taken out of the bath, thoroughly rinsed with cold water and dried at 100° C. Obtained is a green color with very good properties of fastness, especially very good fastness to light, very good fastness to wet processing and very good fastness to peroxide washing.

EXAMPLE 15

In a dyeing cup located in a heatable bath one stirs 0.2 parts of the dyestuff produced according to Example 7 with 0.05 parts of the anion-active wetting agent ® Nekal BX (Supplier: BASF AG, Germany) and 8 parts of a 10% aqueous soda solution. One adds 1.25 parts of a 20% aqueous sodium hydrogen sulfide solution, 0.85 parts of a 45% aqueous sodium tetrasulfide solution and 100 parts of hot water, and one dissolves the dyestuff by boiling. The solution is then diluted with 100 parts of hot water and 4 parts of sodium sulfate are added. In the finished dye liquor in motion 10 parts of cotton material are maintained at 90° C. for 1 hour. The dyed cotton material is then taken out of the liquor and any liquor still adhering to it is squeezed off. Then the dyed material is rinsed thoroughly with cold water. It is immediately placed in a solution at a temperature of 40° C. of 0.23 parts of 35% hydrogen peroxide and 1 part of sodium dihydrogen phosphate in 200 parts of water, which had been previously adjusted to a pH of 8 with caustic soda solution. The dyed cotton material is maintained in motion in the oxidation bath for 15 minutes at 40° C. and it is then taken out of the bath, thoroughly rinsed with cold water and dried at 100° C. Obtained is a green color with very good fastness properties, especially a very good fastness to light, very good fastness to wet processing and very good fastness to washing with peroxide.

EXAMPLE 16

In a dyeing cup located in a heatable bath one stirs 0.4 parts of the dyestuff produced according to Example 7 with 0.05 parts of the anion-active wetting ® Nekal BX (Supplier: BASF AG, Germany), and 10 parts of a 10% soda solution. One adds 2.3 parts of a 20% aqueous sodium hydrogen sulfide solution, 0.85 parts of a 45% aqueous sodium tetrasulfide solution and 100 parts of hot water, and the dyestuff is dissolved by boiling. Then the solution is diluted with 100 parts of hot water and added thereto are 4 parts of sodium sulfate. In the finished dye liquor one maintains in constant motion 10 parts of polyamide yarn at 95° C. for one hour. The dyed polyamide yarn is then removed from the liquor and thoroughly rinsed with cold water. It is immediately placed in a solution at a temperature of 40° C. of 0.45 parts of 35% hydrogen peroxide and 1 part of sodium dihydrogen phosphate in 200 parts of water previously adjusted to a pH of 8 with caustic soda solution. The dyed polyamide yarn is maintained in motion in the oxidation bath for 20 minutes at 40° C., then taken out of the bath, thoroughly rinsed with cold water and dried.

Obtained is a black color with very good fastness properties, especially a very good fastness to light and very good fastness to wet processing.

If Examples 14–16 are carried out using the sulfur dyestuff obtained according to Example 10, one obtains dyeing results which are just as good.

We claim:

1. The process for preparing a condensation product from phenothiazine and p-nitrosophenol in sulfuric acid comprising the steps of (a) oxidizing phenothiazine with at least 0.5 oxidation equivalents of sulphur trioxide or p-nitrosophenol per mole of phenothiazine in 60 to 100% sulfuric acid and then (b) condensing the product of step (a) in 60 to 90% sulfuric acid with p-nitrosophenol whereby a condensation product is obtained which contains at least 60% by weight of the indophenol-S-oxide

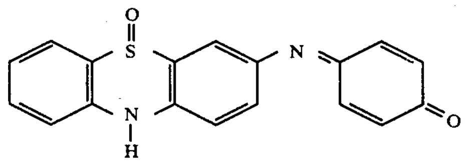

and/or its tautomers.

2. The process of claim 1 wherein the condensation reaction with p-nitrosophenol takes place in 75–82% sulfuric acid.

3. The process of claim 1 wherein for the oxidation reaction of step (a) at least one oxidation equivalent is used per mole of phenothiazine.

4. The process of claim 1 wherein for the oxidation reaction step (a) at least 0.5 mole sulfur trioxide is used per mole of phenothiazine.

5. The process of claim 1 wherein per mole of phenothiazine at least 1.125 mole of p-nitrosophenol is used as oxidizing agent and as condensating agent.

6. The process of claim 1 wherein per mole phenothiazine at least 1.2 mole p-nitrosophenol is used as oxidizing agent and is condensating agent.

7. The product of the process of claim 1.

8. Process for the production of sulfur dyes wherein a condensation product, which contains at least 60% by weight of the indophenol-S-oxide of the formula

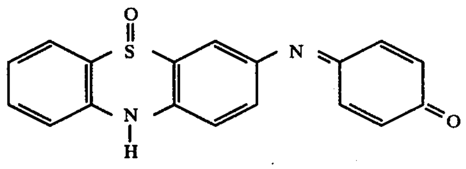

and/or its tautomers or the reduction product thereof, is thionated by the bake or reflux process.

9. The sulfur dyes of the process of claim 8.

10. The process of dyeing fibers containing cellulose or polyamide comprising applying the dyestuff of claim 9 to said fibers.

* * * * *

UNITED STATES PATENT AND TRADEMARK OFFICE

CERTIFICATE OF CORRECTION

PATENT NO. : 4,218,219

DATED : August 19, 1980

INVENTOR(S) : Dr. Gert Nagl

It is certified that error appears in the above-identified patent and that said Letters Patent are hereby corrected as shown below:

| Column | Line | Correction |
|---|---|---|
| 13 | 9 | Change "is condensating agent." to -- as condensating agent.-- |

Signed and Sealed this

*Tenth* Day of *March 1981*

[SEAL]

*Attest:*

RENE D. TEGTMEYER

*Attesting Officer* *Acting Commissioner of Patents and Trademarks*